Figure 1:
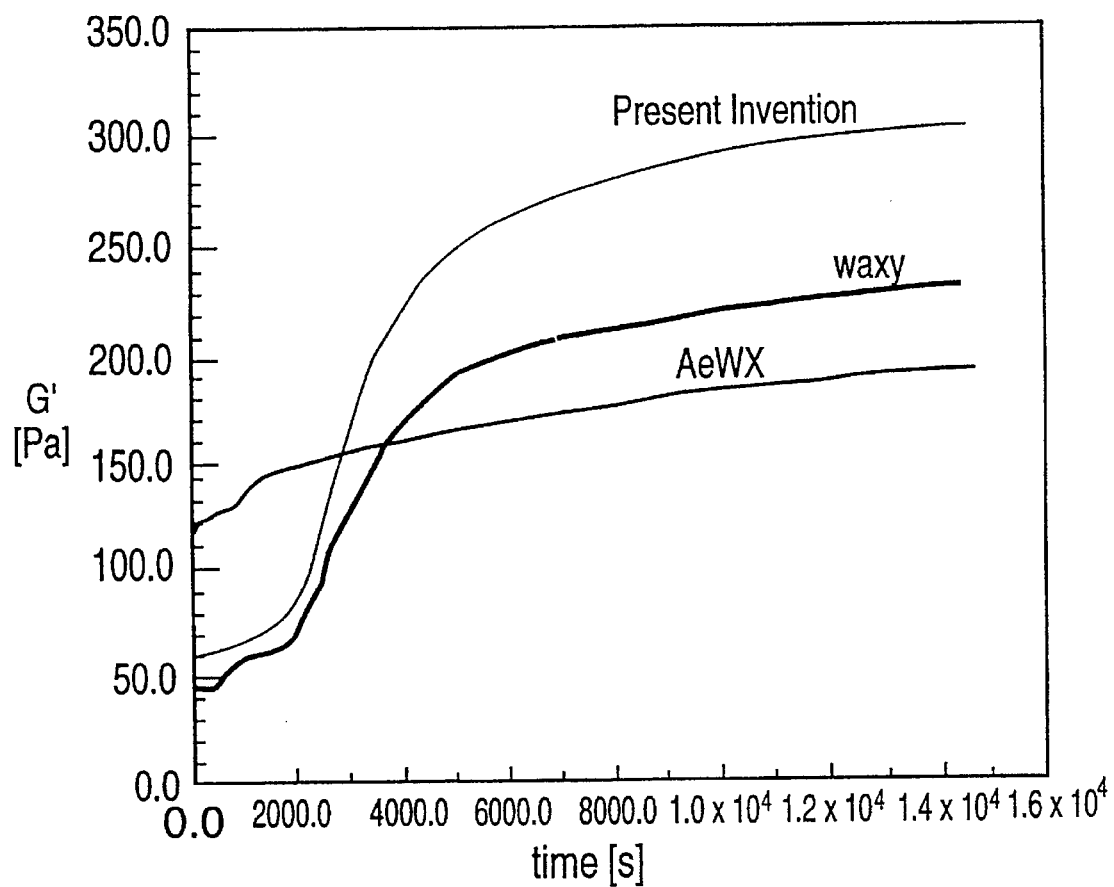

United States Patent [19]

Hauber et al.

[11] Patent Number: 5,576,048
[45] Date of Patent: Nov. 19, 1996

[54] FOODSTUFFS CONTAINING A WAXY WAXY AMYLOSE EXTENDER STARCH

[75] Inventors: Richard Hauber; Robert Friedman, both of Chicago, Ill.; Frances Katz, Crown Point, Ind.

[73] Assignee: American Maize-Products Company, Hammond, Ind.

[21] Appl. No.: 487,466

[22] Filed: Jun. 7, 1995

[51] Int. Cl.⁶ .................................................. A23L 1/0522
[52] U.S. Cl. ........................ 426/578; 426/658; 426/660; 426/661; 536/102; 127/65; 800/235
[58] Field of Search ................................ 426/578, 579, 426/658, 660, 661; 536/102; 127/65; 800/235

[56] References Cited

U.S. PATENT DOCUMENTS

| 4,767,849 | 8/1988 | Friedman et al. | 536/102 |
| 4,770,710 | 9/1988 | Friedman et al. | 127/29 |
| 4,790,997 | 12/1988 | Friedman et al. | 426/578 |
| 4,792,458 | 12/1988 | Friedman et al. | 426/578 |
| 4,798,735 | 1/1989 | Friedman et al. | 426/578 |
| 5,004,864 | 4/1991 | Robertson et al. | 800/235 |
| 5,009,911 | 4/1991 | Mauro et al. | 426/578 |
| 5,300,145 | 4/1994 | Fergason et al. | 106/213 |

FOREIGN PATENT DOCUMENTS 03398  3/1994  WIPO .

OTHER PUBLICATIONS

G. F. Sprague et al. "Corn and Corn Improvement", 1977, Am. Soc. Agronomy, pp. 373–384.
C. A. Neyra "Biochemical Basis of Plant Breeding", vol. 1, Carbon Metabolism, 1985, pp. 133–146.

*Primary Examiner*—Jeanette Hunter
*Attorney, Agent, or Firm*—Lucas & Just

[57] ABSTRACT

A sol and foodstuff containing a substantially pure starch extracted from a starch bearing plant having a waxy, waxy, amylose extender genotype is disclosed. Maize is the preferred plant.

18 Claims, 2 Drawing Sheets

FOODSTUFFS CONTAINING A WAXY WAXY AMYLOSE EXTENDER STARCH

This invention relates to starch and, more particularly, a foodstuff containing a starch which has been extracted from a starch bearing plant having a triple recessive genotype of waxy, waxy, amylose extender (wxwxae).

Starch occurs in a variety of plants and is generally categorized based on its plant source. For example, cereal starches are extracted from cereal grains such as maize, rice, wheat, barley, oats and sorghum; tuber and root starches are extracted from plants such as potato, sweet potato, arrowroot, yams and cassava (tapioca starch); and waxy starches are extracted from plants such as waxy maize, waxy rice, waxy barley and waxy sorghum.

Starch is made up of polymers of anhydroglucose bonded together by both alpha 1–4 and alpha 1–6 bonds. These polymers comprise a majority of alpha 1–4 bonded anhydroglucose units, however, the molecular weight of the polymers and the frequency of the alpha 1–6 bonds varies dramatically based on the genotype of the plant as well as the plant itself from which the starch has been extracted. Needless to say, the growing conditions also have a dramatic effect on the chemical structure of the starch.

It had been discovered that there exists a number of recessive mutant genes in starch bearing plants which have an effect on the properties of starch. By controlled breeding, these mutant genes can be expressed and a myriad of distinctly different starches obtained.

Some of the mutant genes which have been identified in maize include the genotypes: waxy (wx), amylose extender (ae), dull (du), horny (h), shrunken (sh), brittle (bt), floury (fl), opaque (o), and sugary (su). Nomenclature for some of these mutant genes is based in part on the effect these mutant genes have on the physical appearance or phenotype, of the kernel. It is also known that within these genotypes there are genes which produce starches with markedly different functional properties even though the phenotypes appear to be the same. Such subspecies have generally been given a number after the named genotype, for example, sugary-1 (su1) and sugary-2 (su2).

It has been found that certain combinations of these recessive genes can produce surprising and unexpected properties in starch which lead to unique uses of the starch in food products. For example, U.S. Pat. No. 5,009,911 dated Apr. 23, 1991 teaches the use of starch obtained from a plant that has an amylose extender waxy homozygous genotype (aewx), as a thickener in acidic foodstuffs.

It has now been discovered that a starch bearing plant that has a triple recessive genotype with two dosages of waxy and one dosage of amylose extender (i.e. wxwxae) produces a starch which has unique characteristics compared to conventional starch and has properties which make it uniquely suited for use in food. Specifically, it has been found that the starch obtained from plants with this triple dose of recessive genes produces a strong resilient gel which clears from the mouth uniquely fast. The starch of the present invention produces a gel with a unique and distinctive texture compared to conventional starches. The unique and distinctive texture makes the starch of the present invention suitable as a replacement for conventional gelling gums such as natural gums and gelatin, in whole or in part in food formulations. The starch of the present invention has also been found to produce a more resilient gel than common starch. Furthermore, it has been found that cornstarch produced from maize which has the triple recessive wxwxae produces a gel which has improved clarity compared to a gel made from a common starch. Such improved clarity is visible to the human eye and lends itself to a more appetizing foodstuff.

Figure 2:
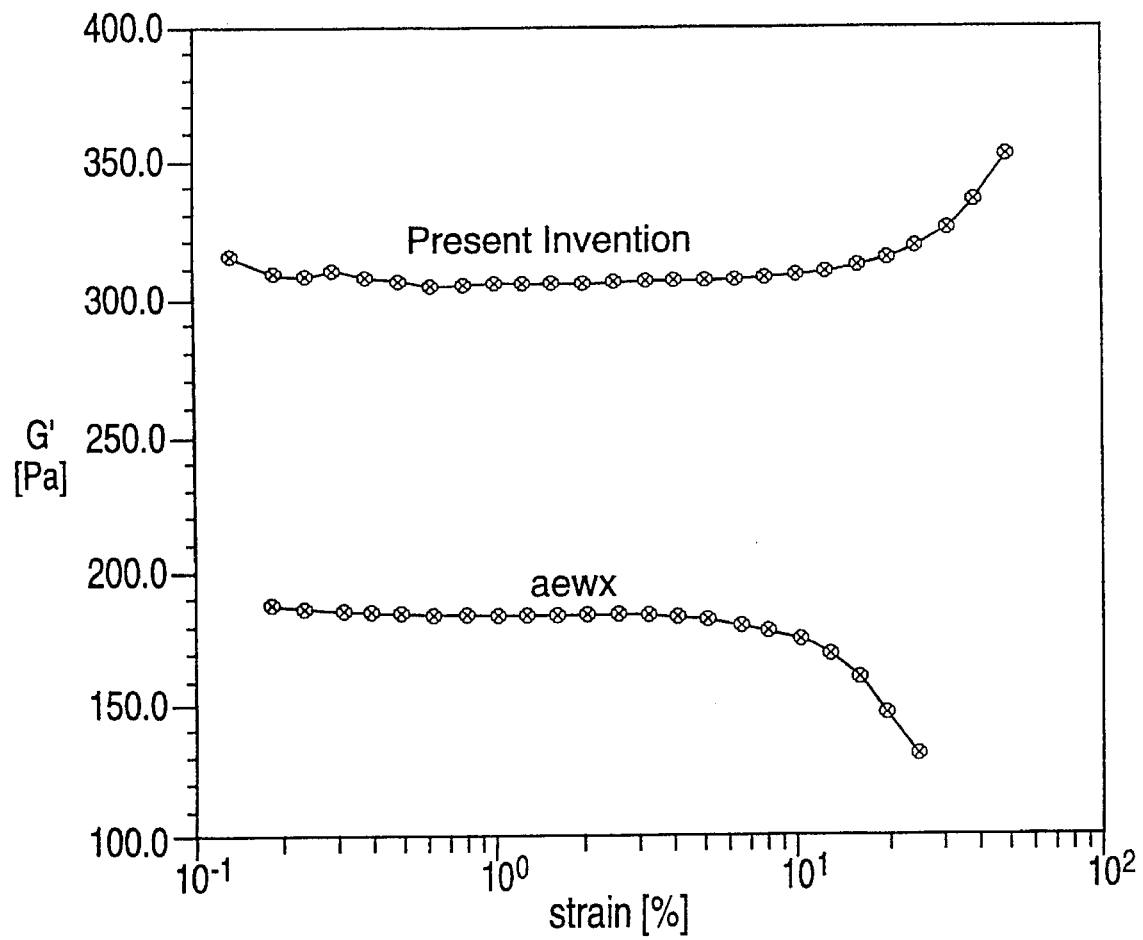

These and other aspects of the present invention may be more fully understood by reference to the following drawings wherein:

FIG. 1 is a plot of the elastic modulus (G') over time comparing a gel made from the starch of the present invention to a gel made from an aewx starch and a gel made from a waxy (wx) starch; and FIG. 2 is a plot of the elastic modulus (G') plotted against strain for both the present invention and an aewx starch.

In order to obtain substantially pure starch in accordance with the present invention, plants which produce edible starch and have either a waxy (wx) or an amylose extender (ae) are crossbred to produce a plant having a waxy, waxy, amylose extender (wxwxae) genotype. The starch is then extracted from the plant. Both the crossbreeding step and the extraction step of the present invention are carried out in a conventional manner. There are also reports of ae modifier genes, see U.S. Pat. No. 5,300,145 issued Apr. 5, 1995. Naturally, these modifier genes can be present in the plant which produces the starch of the present invention so long as they do not materially affect the attributes of the starch of the present invention.

In order to prepare a sol in accordance with the present invention, a slurry is prepared which comprises water and an effective amount of starch extracted from a plant of the wxwxae genotype and the sol subject to a cooking step. The slurry is cooked as necessary to provide a thickener composition. If the starch has been made "cold water swellable", then the cooking step can be eliminated. The preferred amount of starch used in the slurry constitutes about 1 to 20% by weight of slurry. Generally, cooking entails raising the temperature of the slurry to above about the gelatinization temperature of the starch and subjecting the starch to enough shear such that the granules rupture and a paste is formed. It is not necessary that all the granules rupture.

A sol or a thickener composition of the starch of the present invention is added to a foodstuff in a conventional manner in order to provide the benefits of the wxwxae starch to the foodstuff.

Alternatively, starch of the present invention is mixed with a foodstuff in a slurry comprising water and starch of the present invention and the slurry is mixed with foodstuff and the resulting mixture cooked to produce a thickened foodstuff and to provide the benefits of a wxwxae starch to the foodstuff.

In order to replace a gelling gum in food formulations, a weight ratio of about 1:1, starch of the present invention:gelling gum, can be employed. Larger or smaller amounts of the starch of the present invention may be used to replace a gelling gum. Such gelling gums include gelatin, pectin, carrageenan, gum arabic, tragacanth, guar, locust bean, xanthan, agar, algin and carboxymethyl cellulose.

Naturally, the starch of the present invention can be used in any food formulation, where there is a need to provide gel characteristics and a clean break from the mouth. For example, the starch of the present invention can be used in a food formulation which had heretofore employed a common starch, thereby providing the food with improved properties, i.e. clean break when compared to the same food formulation using a common starch.

The term starch as used in the specification and claims means not only the substantially pure starch granules as extracted from a starch bearing plant but also grain products of the starch granule such as flour, grit, hominy and meal.

The term waxy, waxy, amylose extender or wxwxae genotype as used in the specification and claims means not only the wxwxae genotype, i.e. a double dose of recessive waxy (wxwx), single dose of dominate waxy (WX) and a single dose of recessive amylose extender (ae), double dose of dominate amylose extender (AEAE), which has been obtained by standard plant breeding techniques, but also the wxwxae genotype which has been moved to another portion of the plant genome by translocation, inversion or any other method of chromosome engineering to include variations thereof whereby the disclosed properties of the starch of the present invention are obtained.

Any plant source which produces edible starch and which can be crossbred to produce a plant having a wxwxae genotype may be used. Amylose extender (ae) has been found in cereal grains such as maize and barley. Waxy gene has been found in maize, rice, barley and sorghum. Maize is the preferred plant source. The waxy gene is reported to be located on chromosome 9 of the maize chromosomes; amylose extender (ae) is reported to be located on chromosome 5 in maize. These locations are published in the open literature.

Generally, to obtain a starch bearing plant with triple recessive mutants with a double dose of wx and a single dose of ae, conventional plant breeding techniques are employed. It is well known that endosperm tissue is triploid by virtue of receiving two halloid nuclei from the maternal side and one haploid nucleus from the paternal side. The mutations called shrunken-2 (sh2), brittle-2 (bt2), dull (du), sugary (su), waxy (wx) and amylose extender (ae) encode isoforms of ADP glucose pyrophosphorylase, debranching enzyme, soluble starch synthase, bound starch synthase and branching enzyme. The Brittle-2 and Shrunken-2 geno encodes one subunit of DP glucose pyrophosphorylase, the Sugary locus alters expression levels of debranching enzyme and soluble starch synthase, the Waxy gene encodes granule bound starch synthase, whereas the Amylose Extender gene encodes one isoform of branching enzyme, and the Dull gene alters expression of an isoform of soluble starch synthase as well as a debranching enzyme. When these mutants are crossed with wild-type plants, the inheritance patterns of the mutant gene and wild-type gene depends on whether the gene is paternal or maternal in origin. For example in endosperm cells, where there are three doses of each allele, if the mutant is selfed the cells will all inherit 3 mutant genes (mmm). If instead the wild-type plant is used as a source of pollen for the mutant then there will be 2 doses of mutant allele and 1 dose of wild-type allele (mm+). With the mutant as the pollen source, and the wild-type as the female there will be 2 doses of wild-type allele and 1 dose of mutant allele (++m). Selfing the wild type gives 3 wild-type allelles (+++). Significant new starch types are produced by inter-crossing multiple combinations of mutants. Thus, with each mutation the pollen source may be homozygous recessive for one mutant allele while the female may be homozygous recessive for another mutant allele. For example, with the pollen source as waxy mutant (wxwx) and female amylose extender (aeae), the resulting endosperm tissue will be aeae+:wx++.

Known mutants and the gene-dosage crossing regimes have been examined and their effects of altered gene expression on starch deposition in grain. When the mutations are with waxy and amylose extender, changes in starch fine structure (branched chain length changes as well as changes in amylose/amylopectin ratios) have been detected. In these cases there is more minor control of flux to starch and it is the changes in ratios of the starch synthases and branching enzymes which have resulted in alterations in starch fine structure. It is known that not only does the mutation reduce expression of key enzymes, but also it induces an overexpression of other enzymes in the pathway. Furthermore, it is only in the full mutant (mmm) genotypes where the changes in starch fine structure demonstrate that the structural changes occur only when there is an enzyme isoform loss in combination with an enzyme isoform overexpression.

Extraction of starch from the plant is well known and typically entails a milling process. In accordance with the present invention, a wet milling process is used to advantage to extract the corn starch from the corn kernels. Corn wet milling comprises the steps of steeping and grinding the corn kernel and then separating the starch from the other components of the kernel. Prior to steeping, the kernels are subjected to a cleaning process to remove any debris which may be present. This cleaning process is usually done at the wet milling plant. The kernels are then steeped in a steep tank where the kernels are contacted with a countercurrent flow of water at an elevated temperature of about 120° F. and containing sulfur dioxide in an amount between about 0.1 to about 0.2% by weight water. The kernels are maintained in the steep tank for about 24 to 48 hours. Next, the kernels are dewatered and subject to a first set of attrition type mills.

The first set of mills generally grind and rupture the kernels causing the germ, corn oil, to be released from the rest of the kernel. A typical attrition type mill used in commercial wet milling processes is sold under the brand name Bauer. The released germ is then separated from the other parts of the kernel by centrifugation. Throughout the grinding steps of the wet milling process the kernel and the kernel components are maintained in a slurry of about 40% by weight solids.

The remaining kernel components, which include starch, hull, fiber and gluten, are subjected to a second set of attrition type mills such as the Bauer Mill, to further grind the components and separate the hull and fiber from the starch and gluten. Hull and fiber are generally referred to as bran. Washing screens are used to separate the bran from the starch and gluten. The starch and gluten pass through the screens while the bran does not.

Next, the starch is separated from the protein. This step is done either by centrifugation or by a third grind followed by centrifugation. A commercial centrifugation separator suitable for the present process is the Merco centrifugal separator.

The slurry which contains the starch granules is then dewatered and the resulting granules washed with fresh water and dried in a conventional manner preferably to about 12% moisture.

In this manner, the substantially pure starch of the present invention is extracted from a starch bearing plant of the wxwxae genotype.

Alternatively to the drying step, the starch may be left in suspension and subject to further modification.

Modification of the starch may also be performed on the dried starch. Typically, in order to change the physical and/or chemical structure of the starch granule, the starch is subject to any one or more of eight general treatments. These treatments comprise bleaching, thin boiling, acid treatment, enzyme treatment, dextrinization or dry roasting, etherification, esterification, and crosslinking. Starches which have been treated by any one or more of these eight treatments listed above are conventionally referred to as chemically modified starches.

Bleaching, often referred to as oxidation, is a modification which does not appreciably alter the granular structure of the starch. Oxidation does, however, tend to lighten the color of the granules and reduce the viscosity of the starch paste.

In order to bleach the starch of the present invention, a slurry of starch is prepared of about 5 to about 40% by weight starch. To the slurry sodium hypochlorite is added with about 6% available chlorine (free chlorine) and the slurry is held at about 110° F. for between about 1 to about 20 hours. The slurry is then neutralized with sodium bisulphite and the resulting granules are dewatered, washed and dried in a conventional manner.

Such modification makes the starch of the present invention suitable for laundry starch, paper coating and as a textile size.

In order to produce a thin boiled starch of the present invention, a slurry of starch is prepared of about 5 to about 40% by weight starch. To this slurry, a mineral acid is added and allowed to react with the starch for about 1 to about 100 hours at about 90° to about 120° F. with constant agitation. Such a reaction is done below the gelatinization temperature of the starch. Subsequently, the solution is neutralized, dewatered, washed and dried in a conventional manner.

Thin boiling leaves the granules intact and produces a starch product which has a slight reduced viscosity compared to the non thin boiled starch. If partial or total destruction of the starch granule is sought, the granule may be subjected to acid treatment.

In order to acid treat the starch of the present invention, a slurry of starch about 5 to about 40% by weight starch is prepared. This slurry is reacted with acid, generally a strong acid, at a temperature above gelatinization temperature. Such a procedure is preferably carried out by jet cooking the slurry through a conventional jet cooker with or without acid already in the slurry and then allowing the slurry to react with the acid, adding acid if needed, for a desired period of time or until the desired dextrose equivalent (DE) is reached. The DE is roughly proportional to the length of time for the reaction. Generally, such jet cooking destroys the starch's granular structure.

After acid treatment, the resulting slurry is neutralized, dewatered and dried. Such product may also be subject to conventional carbon treatment and filtration prior to dewatering and drying. Another treatment which degrades the granular structure is enzyme treatment.

In order to enzyme treat the starch of the present invention, a slurry of starch is made up having about 5 to about 40% by weight starch. To this slurry, an enzyme is added at the optimum pH and temperature for the enzyme. Some advantage is found by first jet cooking the slurry to open up the starch granules, cooling the slurry to optimum temperature for the enzyme and then adding the enzyme. If the enzyme is jet cook stable then the enzyme can be added to the slurry prior to jet cooking. The slurry may also be treated with acid first to a low DE and then enzyme treated. After enzyme treatment, the product is dewatered and dried. Alternatively, the product may be subject to conventional carbon bleaching and filtration prior to concentration and/or drying.

In order to dextrinize or dry roast the starch of the present invention, acid is added to dry starch granules and the mixture is heated to a temperature of about 250° to about 350° F. for about 3 to about 72 hours. The product, once removed from the heat, is sold as is. The preferred acids are hydrochloric, phosphoric and any mineral acid. Such a method causes the partial breakdown of the granular structure.

In order to etherify the starch of the present invention, a slurry of starch is made up having about 5 to about 40% by weight starch. The pH of the slurry is adjusted to about 10 to about 12 preferably with sodium hydroxide. Next, an etherification agent such as ethylene oxide or propylene oxide is added to the slurry in an amount of about 0.5 to about 25% depending on the desired degree of substitution. The reaction conditions are held for about 5 to about 30 hours at about 70° to about 120° F. The slurry is then neutralized with any known acid, dewatered, washed and dried.

In order to crosslink the starch of the present invention, a slurry of starch is made up of about 5 to about 40% by weight starch. The pH of the slurry is adjusted to about 8 to about 12 preferably with sodium hydroxide. Optionally, a salt may be added to the slurry to affect swelling of the granules. Then the slurry is reacted with a crosslinking agent such as phosphorous oxychloride, trimethaphosphate salt, adipic acid or epichlorohydrin at about 70° to about 120° F. for about ½ to about 5 hours. The length of time of the reaction will depend on the amount of crosslinking agent used and the specific crosslinking agent chosen.

In order to esterify the starch of the present invention, a slurry of starch is prepared having about 5 to about 40% by weight starch. The pH of the slurry is then adjusted to about 8 to about 10 and an esterification agent is added to the slurry such as vinyl ester, adipic acid acetyl halides, acid anhydrides like acetic anhydride, succinic anhydride or derivatives of such anhydrides. The esterification agent is added slowly while maintaining the pH of the slurry. The reaction is continued for about ½ to about 5 hours at about 80° to about 120° F. Once the reaction is completed to the desired degree of substitution, the slurry is neutralized, dewatered, washed and dried.

Any combination of these modifications may be employed on starch of the present invention.

It has been found that a sol comprising water and an effective amount of starch extracted from a plant of a wxwxae genotype exhibits thickening characteristics which makes the sol a good commercial thickener composition. Such thickener compositions are especially useful in foodstuffs.

The sol is prepared by forming a slurry of water and starch of the present invention and subsequently cooking the slurry thereby forming a paste. Preferably, the sol contains the starch of the present invention in the amount of about 1 to about 20% by weight total sol. The slurry is cooked at a temperature of about 90° C. and above to provide thickening characteristics prior to adding to the foodstuff. Cooking time is about 10 minutes. The sol in accordance with the present invention need not be cooked if the starch has already been subjected to a process which makes it cold water swellable. Cooking generally comprises raising the temperature of an aqueous slurry of the starch of the present invention to the gelatinization temperature of..the starch and subjecting the starch to shear such that the starch granules rupture and form a paste.

In order to prepare the thickened foodstuff, a sol made in accordance with the present invention is combined with a foodstuff and the composition is cooked to the necessary degree to provide a thickened foodstuff. Conventional mixing is employed to combine the sol with the foodstuff. Cooking of the sol and foodstuff composition is also carried out in a conventional manner.

Alternatively, starch of the present invention is mixed with the foodstuff or a slurry comprising the starch of the present invention and water is mixed with a foodstuff and the resulting mixture is cooked to the desired degree to obtain a thickened foodstuff. When the starch itself or a slurry containing the starch itself is mixed with a foodstuff, the resulting mixture must be cooked in order to provide a thickened foodstuff. The mixing as well as the cooking is accomplished in a conventional manner. Cooking is carried out at a temperature of about 90° C. and above. Cooking time is about 10 minutes but may vary depending on the amount of foodstuff present and the amount of shear that the mix is subject to during cooking.

Such a thickener composition can provide considerable economic advantage to the user. Those familiar with the art have long used a variety of gelling gums for their clean breaking texture. Application of the present invention have included but are not limited to gum candies, gelled desserts, glazes and spreads and can be used to replace conventional gelling gums such as kappa carrageenin, agar, pectin, or gelatin. These conventional gelling gums can be quite expensive however, and have other disadvantages including the presence of off-flavors, lack of heat or acid stability, limited availability, or lack of Kosher approval. It has been found that the starch of the present invention can replace all or a portion of these conventional gelling gums.

The clean break of a gel made with the starch of the present invention is useful in a variety of food applications. The clean break of the starch gel has value in a variety of bakery applications, for example cream or fruit fillings for pies such as lemon, banana cream or Bavarian cream; and in low or reduced fat high solids fruit centers for cookies, for example, in fig bars. The starch of the present invention also creates an improved texture in mousses, egg custards, flans and aspics.

These and other aspects of the present invention may be more fully understood with reference to the following examples.

EXAMPLE 1

This example illustrates the extraction of the starch of the present invention from a wxwxae maize kernel produced by conventional breeding techniques and tests the starch to determine its various characteristics. The tests as well as the results obtained therefrom are given in Table I below. The extraction process as well as the test procedures followed are outlined following Table I below:

TABLE I

| Test | Present Invention |
| --- | --- |
| Percent Protein (dry basis) | 0.39% |
| Percent Oil (dry basis) | 0.09% |
| Percent Amylose (starch basis) | 21.1% |
| DSC Gelatinization Temp. | 72.9° C. |
| Regular Brabender Amylograms | |
| Initial Rise | 74° C. |
| Heating Peak | 360 BU |
| Heating Final | 355 BU |
| Cooling Peak | 590 BU |
| Cooling Final | 460 BU |
| Brookfield Viscosity (20 RPM) | 5,600 cps. |

Extraction Process

The following extraction process was used to extract the starch from kernels obtained from maize having a wxwxae genotype.

Steeping

Steeping was carried out by adding maize kernels to water having a 0.2% $SO_2$ content and holding the temperature of the steep water at 50° C. for 48 hours. The steep water was circulated through the steep container. After the 48 hours of steeping, the kernels were dewatered and washed with water.

It will be appreciated by those of skill in the art that there are other known methods for steeping corn including pressure and enzyme and that the claims are not to be limited to any one method.

Grinding and Separating

A mixture of 1:1 kernels to water in a weight ratio was prepared and added to a Waring blender equipped with a dull blade. The Waring blender was put on grind for one minute to mill the starch. The resulting mash was poured onto a 40 mesh screen and what passed through the 40 mesh screen was passed through a 200 mesh screen and subsequently through a 325 mesh screen. The resulting filtrate contained starch and protein. That which did not pass through the first 40 mesh screen was put pack into the Waring blender with water in a 1:1 weight ratio. This time a sharp blade was used and the Waring blender was set for one minute on grind. The resulting mash was then subject to a 40 mesh screen and then the filtrate was subjected to a 200 mesh screen and finally to a 325 mesh screen. The final filtrate from both the dull blade grind and the sharp blade grind were dewatered and contained starch and protein. The starch and protein were reslurried and subjected to up to three separate centrifugation to separate the starch from the protein.

The final starch was then filtered and dried in an oven at 110° C. overnight to a moisture content of approximately 10%.

In this manner, starch was extracted from corn kernels in the lab.

The percent protein was determined by a standard Corn Refiners Association (CRA) method (Kjeldahl method).

The percent oil was also done using a standard CRA method by extracting the oil from dry, ground kernels using carbon tetrachloride for 16 hours.

The percent amylose was determined using standard calorimetric iodine procedures wherein the starch is first gelatinized with sodium hydroxide and then reacted with an iodine solution and the resulting sample measured using a spectrophotometer in a 1 cm cell at 600 nm against a blank of 2% iodine solution.

The DSC gelatinization temperature was measured using a scanning calorimeter manufactured by Mettler Model No. 300 using 30% starch solids following the procedure outlined in the owner's manual for that model.

The Brabender amylogram was run at 5.5% solids using a 460 gram sample with 125 gram cartridge at 100 RPM. The exact procedure used is outlined in the Amylograph Handbook of the American Association of Cereal Chemists, 1982 Edition on pages 17 and 18. The respective paddle for the 460 gram cup was used.

The initial rise was the temperature at which the pen moves away from the baseline.

The sample measurements started at room temperature and the rapid heat mode of the instrument was used to heat the sample to 50° C. Once 50° C. was reached, the instrument was set at a controlled rate of heating, 1½° C./minute, until a temperature of 95° C. was reached. The sample was then held at 95° C. for 30 minutes. During this period of heating, the highest viscosity obtained by the sample was labeled Heating Peak. The Heating Final was the last viscosity obtained by the sample at the end of the heating cycle. Next, the sample was cooled at 1½° C. to a temperature of 50° C. The sample was then held at 50° C. for 30 minutes. The largest viscosity measurement taken during this cooling cycle was the Cooling Peak and the final viscosity at the end of the cooling cycle was the Cooling Final.

Brabender curves are a well known tool for determining characteristics of starch.

Brookfield viscosities, another well known measurement used for analyzing starch was measured for the starch of the present invention in Table I above. In order to run this test, a Brookfield viscometer Model RV was used following standard procedures to obtain these values. This test was run at 50° C. at 20 RPM.

EXAMPLE 2

This example illustrates the gelatinization temperature of the starch of present invention compared to other starches. The gelatinization temperatures are listed in Table II below.

TABLE II

| Starch Samples | % Amylose* | Gelatinization* Temperature °C. |
|---|---|---|
| 1. Native common maize | 28 | 71 |
| 2. AMY V native | 57 | 80 |
| 3. AMY VII native | 73 | 90 |
| 4. Native wxwxae | 21 | 73 |
| 5. Native aewx | 25 | 80 |
| 6. Native wxwxwx | 3 | 72 |

*Values rounded to a whole number

Sample 1 was a commercial product sold by American Maize-Products Company of Hammond, Indiana. The percent amylose and the gelatinization temperature for Sample 1 above are mean values determined by random sampling of product. The 99% confidence level for percent amylose and gelatinization temperature are 25.9 to 29.3 and 68.7 to 72.9, respectively.

AMY V and AMY VII are commercial high amylose corn starches sold by American Maize-Products Company of Hammond, Ind. The percent amylose and the gelatinization temperatures in Table II above are mean values determined from a random sampling of product. The 99% confidence interval for the percent amylose in AMY V and AMY VII was 53.4 to 62.5 and 65.5 to 73.8, respectively. The 99% confidence interval for the gelatinization temperature for AMY V and AMY VII was 72.8 to 84.4 and 83.1 to 90.8, respectively. Both AMY V and AMY VII were grown in native maize.

Starch Sample 4 corresponds to the Sample of Example 1 above, while Sample 5 corresponds to the average values from Example 1 of U.S. Pat. No. 5,009,911. Sample 6 corresponds to a commercial waxy starch sold by American Maize-Products Company.

The method for determining both the percent amylose and the gelatinization temperature was that outlined in Example 1 above.

It is readily apparent from Table II above that the gelatinization temperature of the starch of the present invention is comparable to common corn starch.

EXAMPLE 3

This example illustrates the gel strength of a sol made from the corn starch of the present invention compared to a sol made from aewx corn starch, a sol made from common corn starch, and a sol made from wxwxwx starch. The results of the test are reported in Table III below.

TABLE III

| Sample | Strength (grams) |
|---|---|
| Present Invention (wxwxae) | 159.5 |
| Common Corn Starch | 225.0 |
| aewx Corn Starch | 55.0 |
| Waxy Corn Starch (wxwxwx) | 16.0 |

In order to perform the gel strength test reported in Table III above, sols were prepared by mixing water with starch and subjecting the slurry to a rapid heat mode in the Brabender Visco-Amylograph to heat the sample to 50° C. Once 50° C. was reached, the instrument was set at a controlled rate of heating, 1.5° C./minute, until a temperature of 95° C. was reached. The sample was then held at 95° C. for 30 minutes. Next, the sample was cooled at 1.5° C. to a temperature of 50° C. The sample was then held at 50° C. for 30 minutes. Portions of these sols were added separately to 4 ounce jars into which a plunger was placed. The sols were then allowed to stand at ambient conditions for 24 hours. Gel strength was measured by determining the force needed to remove the plunger from the sol.

This example illustrates that the gel strength of a sol made in accordance with the present invention is comparable to common corn starch sols.

EXAMPLE 4

This example illustrates the difference between aewx starch, a waxy starch wherein the plant had a triple dose of the waxy gene, and wxwxae starch of the present invention. All starches were obtained from maize.

All starches were tested for their rheological properties. Each starch was subjected to the same test procedure using the same method. The starch granules were pasting using a Brabender Visco-Amylograph with the cooling probe down and with the 750 g cm cartridge. The starch slurry, 5.5% initial solids, was rapidly heated to 60° C. in the Brabender cup, and then pasted while increasing the temperature to 95° C. at 1.5° C. per minute. The starch paste was held at this temperature for 20 minutes, and then immediately loaded onto the measuring geometry of the rheometer which had been preheated to 70° C. A four-part rheological characterization was performed. The gel cure segment which monitored the formation of structure at 0.2 hertz and 0.2% strain (well within the linear viscoelastic region) was measured as the sample was cooled from 70° C. to 25° C. and held for 4 hours. Also measured was the strain sweep, which measures the rheological response of the paste or gel to increasing levels of strain, also at 0.2 hertz, at 25° C.

Using this technique, distinct differences between aewx starch and the starch of the present invention were found. FIG. 1 shows the results of the gel cure analysis. The starch of the present invention, while having an initial Modulus (G') lower than aewx starch, more quickly formed structure or gelled as evidenced by the rapid rise in G'. Thus the starch of the Present Invention was distinct from aewx starch in the rate of gel formation despite similar apparent iodine binding contents. FIG. 2 shows the results of the strain sweep analysis only for the starch of the present invention and the aewx starch. Here the starch of the present invention showed dilatant behavior as evidenced by the increase in G' as the strain level was increased. Under the applied levels of strain, the structure was not destroyed. In contrast, the structure of the aewx starch was rapidly destroyed when the applied strain became greater than 4%. Thus, when compared to aewx starch, the starch of the present invention formed a gel which didn't break under the applied strain of this test. In contrast, aewx starch showed much less time-dependent structure formation and did "break" or was destroyed by the strains applied in this technique.

EXAMPLE 5

This example compares Brabender curves for aewx starch, a waxy starch and wxwxae starch. Table IV below lists the values obtained.

TABLE IV

|  | wxwxae | aewx | wxwxwx |
|---|---|---|---|
| Regular Brabender Amylograms |  |  |  |
| Initial Rise (°C.) | 74 | 86 | 71 |
| Heating Peak (Bu) | 360 | 238 | 570 |
| Heating Final (Bu) | 355 | 238 | 200 |
| Cooling Peak (Bu) | 590 | 310 | 280 |
| Cooling Final (Bu) | 460 | 310 | 280 |
| Brookfield Viscosity |  |  |  |
| 20 RPM (cps) | 5,600 | 3,175 | 2,225 |

The wxwxae starch data was taken from Example 1 while the aewx starch data was an average of Sample A and Sample B as reported in U.S. Pat. No. 5,009,911, and then rounded to the nearest whole number. The wx starch data is typical of commercial waxy starch sold by American Maize-Products Company.

As can be seen from the data, the added pair of recessive waxy genes to the wxwxae starch is not equivalent to a numerical average of the aewx starch and wx starch. For example, the Brookfield viscosity of wxwxae starch is double the Brookfield viscosity of the aewx starch and three times the Brookfield viscosity of the wx starch.

This illustrates the surprising and unexpected results obtained from the second dosage of the waxy gene. The Brookfield viscosities were run in accordance with the procedure in Example 1, above.

EXAMPLE 6

This example illustrates preparing a thickener composition in accordance with the present invention.

The starch of the present invention as extracted in Example 1 above is mixed with water in an amount to produce a slurry having 10% by weight starch. The sol has a short texture and a bland taste. The sol when cooked at about 90° C. for 10 minutes produces a thickener composition which had better clarity than a similar thickener composition made from common corn starch and a shorter texture.

EXAMPLE 7

This example compares the mouth feel of a gel made from the starch of the present invention to a gel made with a common starch.

The common starch and starch of the present invention were pasted using a Brabender visco-amylograph. The starch was slurried at 5.5% solids, and then heated using the rapid heat mode to 50° C. Using controlled heat of 1.5° C. per minute the slurries were heated to 95° C., and then held at this temperature for 30 minutes. The final solids was 5.9%. The sample starch pastes were then poured into small jelly jars, covered with cellophane, and allowed to age 24 hours before analysis. A taste panel was then asked to rank the samples for the following attributes.

First they ranked the two for relative firmness to the touch.

| Common | Present Invention |
|---|---|
| 5.1 | 5.6 |

Next, they ranked the relative break, firmness, and clearing of this sample while being masticated.

|  | Common | Present Invention |
|---|---|---|
| Degree of clean break | 3.2 | 8.5 |
| Firmness | 4.4 | 4.5 |
| Rate of clearing | 2.5 | 4.6 |

These results show that the firmness of these samples is similar. However the starch of the present invention has a much cleaner break while being masticated. Furthermore, it tends to clear from the mouth faster than a common based starch gel. The panel all agreed that the starch of the present invention produced a gel which had a "clean" mouth feel similar to that of a gelatin or a pectin.

EXAMPLE 8

This example illustrates making a gum candy using the starch of the present invention.

The following ingredients and procedure are used:

TABLE V

| Ingredients | % by Weight Present Invention |
|---|---|
| 44/62 Corn Syrup Unmixed | 56.34 |
| Sugar, fine granular | 23.98 |
| Water | 7.73 |
| Present Invention Starch | 11.80 |
| Citric Acid | 0.07 |
| Sodium Citrate | 0.08 |
|  | 100.00 |

Procedure

All ingredients are mixed and then cooked to 340° F. using conventional equipment such as a jet cooker. The cooked slurry is then poured into candy molds and allowed to solidify.

EXAMPLE 9

This example illustrates making a Bavarian cream pie using starch of the present invention.

The following ingredients and procedure are used:

TABLE VI

| Ingredients | % by Weight Present Invention |
|---|---|
| Whole milk, fresh 3.5% | 72.794 |
| Sugar, fine grain | 17.586 |
| Salt, Flour | 0.101 |
| Present Invention | 5.410 |
| Banana Flavoring | 0.300 |

TABLE VI-continued

| Ingredients | % by Weight Present Invention |
|---|---|
| Egg Yolk, fresh | 3.809 |
| | 100.000 |

Procedure

All of the pie filling ingredients except for egg yolks are combined and cooked at 195° F. for 3 to 5 minutes. Then the ingredients are cooled to 120° F. with constant stirring. Next, egg yolks are added and the admixture well blended. This mixture is then added to a conventional pie crust and allowed to cool to room temperature before serving.

EXAMPLE 10

This example illustrates preparing a lemon pie filling with the starch of the present invention.

The following ingredients and procedure are used:

TABLE VII

| Ingredients | % By Weight Present Invention |
|---|---|
| Water | 62.94 |
| Sugar | 19.30 |
| Maltodextrin | 6.67 |
| Present Invention | 4.50 |
| Corn Syrup Solids | 2.50 |
| Lemon Juice | 2.50 |
| Vegetable Shortening | 1.03 |
| Salt | 0.23 |
| Citric Acid | 0.20 |
| Emulsifier | 0.10 |
| Lemon Oil (2x) | 0.03 |
| | 100.00 |

Procedure

Half of the water is combined with the sugar and brought to a boil. All of the remaining ingredients are slurried together and then added to the boiling sugar and water. The temperature of this mixture is then adjusted to 200° F. and held there for two minutes. The mixture is then poured into prepared pie crusts and allowed to cool and solidify.

The starch of the present invention is obtained in accordance with Example 1 above.

EXAMPLE 11

This example illustrates making a chocolate mousse using the starch of the present invention. The formulation in Table VIII is employed to prepare a mousse mix.

TABLE VIII

| | % |
|---|---|
| Frodex 24–924 | 39.20 |
| Sugar (Baker's) | 30.75 |
| Whiptreme 3554 (Kerry Ingredients) | 12.88 |
| Starch of Present Invention | 9.80 |
| Cocoa, Dutch Red (Gill & Duffus Products) | 7.17 |
| Lecceitreme 40 (Kerry Ingredients) | 0.20 |
| Flavor | as desired |
| | 100.00 |

Procedure

Combine ingredients to form a uniform blend.

Use

Combine 200 gms. of mousse mix with 1 cup (250 grs.) milk. Using an electric mixer, combine on low speed for 1 minute. Scrape bowl. Mix on high speed for 3 minutes, until light and fluffy. Spoon into serving dishes and refrigerate for 1 hour before serving.

To prepare the mousse mix, all the ingredients are mixed. To prepare the mousse itself, 200 grams of mousse mix are combined with 250 grams of milk and combined at a low speed. Then the mixture is stirred at a high speed to make it light and fluffy and the mixture is refrigerated for one hour. In this way, a light, fluffy mousse is prepared.

It will be understood that the claims are intended to cover all changes and modifications of the preferred embodiments of the invention herein chosen for the purposes of illustration which do not constitute a departure from the spirit and scope of the invention.

What is claimed is:

1. A sol comprising water and an effective amount of a starch extracted from a starch bearing plant having a waxy, waxy, amylose extender genotype.

2. The sol of claim 1 wherein the starch is present in an amount of about 1% to about 20% by weight.

3. The sol of claim 1 wherein the plant is maize.

4. The sol of claim 1 wherein the starch is cold water soluble.

5. The sol of claim 1 wherein said starch is in granular form.

6. The sol of claim 4 wherein said starch is extracted from maize.

7. A foodstuff comprising a foodstuff and having as an essential ingredient therein an effective amount of a starch extracted from a starch bearing plant having a waxy, waxy, amylose extender genotype.

8. The foodstuff of claim 7 wherein said starch is present in an amount of about 0.1% to about 10% by weight foodstuff.

9. The foodstuff of claim 7 wherein said starch is extracted from maize.

10. A method for making a sol containing starch comprising the steps of:

forming a slurry comprising water and an effective amount of a starch extracted from a starch bearing plant having waxy, waxy, amylose genotype; and cooking said starch to gelatinize said starch.

11. The method of claim 10 wherein said effective amount is about 1% to about 20% by weight slurry.

12. The method of claim 10 wherein said starch is extracted from maize.

13. A method for thickening a foodstuff comprising the steps of:

combining with a foodstuff an effective amount of a starch extracted from a starch bearing plant having a waxy, waxy, amylose extender genotype; and cooking said foodstuff to thicken said foodstuff.

14. The method of claim 13 wherein said starch is extracted from maize.

15. The method of claim 13 wherein said starch is present in an amount of from about 0.1% to about 10% by weight of said foodstuff.

16. An improved method for making a foodstuff which contains a gelatin said improvement comprising replacing at least a portion of the gelatin in said foodstuff with the sol of claim 1.

17. An improved method for making a foodstuff which contains a natural gum, said improvement comprising replacing at least a portion of the natural gum with the sol of claim 1.

18. The method of claim 17 wherein said foodstuff is a gum candy, a gelled dessert, a glaze, or a spread.

* * * * *

UNITED STATES PATENT AND TRADEMARK OFFICE
CERTIFICATE OF CORRECTION

PATENT NO.   : 5,576,048
DATED        : November 19, 1996
INVENTOR(S)  : Richard Hauber et al.

It is certified that error appears in the above-indentified patent and that said Letters Patent is hereby corrected as shown below:

Column 8, line 55, change "moves" to --moved--.

Column 9, line 6, after "starch", insert --,--.

Column 10, line 36, change "pasting" to --pasted--;
line 58, change "Present Invention" to --present invention--.

Column 14, line 52 (claim 10) change "starch" (first instance) to --slurry--.

Signed and Sealed this

Eighteenth Day of February, 1997

Attest:

BRUCE LEHMAN

*Attesting Officer*   *Commissioner of Patents and Trademarks*